(12) United States Patent
Ellingson

(10) Patent No.: US 8,983,606 B2
(45) Date of Patent: Mar. 17, 2015

(54) ENHANCED SENSING BY AN IMPLANTABLE MEDICAL DEVICE IN THE PRESENCE OF AN INTERFERING SIGNAL FROM AN EXTERNAL SOURCE

(75) Inventor: Michael L. Ellingson, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 927 days.

(21) Appl. No.: 12/915,233

(22) Filed: Oct. 29, 2010

(65) Prior Publication Data

US 2012/0108908 A1   May 3, 2012

(51) Int. Cl.
*A61N 1/37* (2006.01)
*A61B 5/04* (2006.01)

(52) U.S. Cl.
CPC ........... *A61N 1/3704* (2013.01); *A61B 5/04005* (2013.01); *A61N 1/3718* (2013.01)
USPC .................................. 607/31; 607/30; 607/59

(58) Field of Classification Search
CPC .............. A61N 1/3718; A61N 1/3704; A61B 5/04005; A61B 5/04007; A61B 5/04008
USPC .................................. 607/30, 31, 59; 128/901
See application file for complete search history.

(56) References Cited

U.S. PATENT DOCUMENTS

| | | | |
|---|---|---|---|
| 5,003,975 A | 4/1991 | Hafelfinger et al. |
| 5,197,468 A | 3/1993 | Proctor et al. |
| 5,217,010 A | 6/1993 | Tsitlik et al. |
| 5,438,990 A | 8/1995 | Wahlstrand et al. |
| 5,513,644 A | 5/1996 | McClure et al. |
| 5,662,694 A | 9/1997 | Lidman et al. |
| 5,697,958 A | 12/1997 | Paul et al. |
| 5,718,242 A | 2/1998 | McClure et al. |
| 5,722,998 A | 3/1998 | Prutchi et al. |
| 5,741,311 A | 4/1998 | McVenes et al. |
| 6,101,417 A | 8/2000 | Vogel et al. |
| 6,112,119 A | 8/2000 | Schuelke et al. |
| 6,134,430 A | 10/2000 | Younis et al. |
| 6,151,400 A | 11/2000 | Seligman |
| 6,421,555 B1 | 7/2002 | Nappholz |
| 6,584,351 B1 | 6/2003 | Ekwall |
| 7,076,283 B2 | 7/2006 | Cho et al. |
| 7,082,328 B2 | 7/2006 | Funke |

(Continued)

OTHER PUBLICATIONS (PCT/US2011/055951) PCT Notification of Transmittal of the International Search Report and the Written Opinion of the International Searching Authority.

(Continued)

*Primary Examiner* — Tammie K Heller
(74) *Attorney, Agent, or Firm* — Michael J. Ostrom; Stephen W. Bauer

(57) ABSTRACT

An implantable medical device (IMD) adjusts a sensing configuration of a sensing module prior to or immediately subsequent to entering an environment having an external source that generates the interfering signal. The IMD may, for example, adjust a sampling frequency, resolution, input range, gain, bandwidth, filtering parameters, or a combination of these or other sensing parameters of the sensing module. These adjustments enable the sensing module to obtain a more detailed representation of the sensed signals, including the noise components of the sensed signals caused by the interfering signal. Without having an adequate representation of the noise components of the sensed signal, it is difficult to separate the noise components of the sensed signal from the cardiac electrical signal.

27 Claims, 5 Drawing Sheets

(56) References Cited

U.S. PATENT DOCUMENTS

| | | |
|---|---|---|
| 7,231,251 B2 | 6/2007 | Yonce et al. |
| 7,242,981 B2 | 7/2007 | Ginggen |
| 7,369,898 B1 | 5/2008 | Kroll et al. |
| 7,783,354 B2 | 8/2010 | Gunderson |
| 7,917,212 B2 | 3/2011 | Yonce et al. |
| 8,014,856 B2 | 9/2011 | Wedan |
| 8,014,867 B2 | 9/2011 | Cooke et al. |
| 8,090,445 B2 | 1/2012 | Ginggen |
| 8,160,717 B2 | 4/2012 | Ameri |
| 8,335,563 B2 | 12/2012 | Stessman |
| 8,433,408 B2 | 4/2013 | Ellingson et al. |
| 8,509,888 B2 | 8/2013 | Linder et al. |
| 8,543,207 B2 | 9/2013 | Cooke et al. |
| 8,554,335 B2 | 10/2013 | Ameri et al. |
| 8,571,661 B2 | 10/2013 | Stubbs et al. |
| 2001/0044641 A1 | 11/2001 | Eberle et al. |
| 2002/0147468 A1 | 10/2002 | Kim et al. |
| 2003/0083570 A1* | 5/2003 | Cho et al. .............. 600/410 |
| 2003/0083713 A1 | 5/2003 | Palreddy et al. |
| 2003/0097157 A1 | 5/2003 | Wohlgemuth et al. |
| 2003/0144705 A1 | 7/2003 | Funke |
| 2004/0162591 A1 | 8/2004 | Jorgenson et al. |
| 2006/0167496 A1 | 7/2006 | Nelson et al. |
| 2006/0264777 A1 | 11/2006 | Drew |
| 2006/0293591 A1 | 12/2006 | Wahlstrand et al. |
| 2007/0238975 A1 | 10/2007 | Zeijlemaker |
| 2008/0071168 A1 | 3/2008 | Gauglitz et al. |
| 2008/0228092 A1 | 9/2008 | Wedan |
| 2010/0023084 A1 | 1/2010 | Gunderson |
| 2010/0106215 A1 | 4/2010 | Stubbs et al. |
| 2011/0160602 A1 | 6/2011 | Stubbs et al. |

OTHER PUBLICATIONS

Naehle, Claas P. et al; "Magnetic Resonance Imaging at 1.5-T in Patients With Implantable Cardioverter-Defibrillators"; Journal of the American College of Cardiology; vol. 54, No. 6, 2009; pp. 549-555.

* cited by examiner

ENHANCED SENSING BY AN IMPLANTABLE MEDICAL DEVICE IN THE PRESENCE OF AN INTERFERING SIGNAL FROM AN EXTERNAL SOURCE

TECHNICAL FIELD

The disclosure relates generally to implantable medical devices and, in particular, to sensing by implantable medical devices in the presence of an interfering signal from an external source.

BACKGROUND

A wide variety of medical systems are implanted within patients to provide a therapy to and/or monitor a physiologic condition of a patient. These implantable medical systems may include an implantable medical device (IMD) and one or more implantable medical leads to deliver therapy to or monitor conditions of a number of organs, nerves, muscles or tissues of the patient, such as the heart, brain, stomach, spinal cord, pelvic floor or the like.

Occasionally, patients that have implantable medical systems may benefit from a medical procedure that may generate an interfering signal. For example, a patient may benefit from a magnet resonance image being taken of a particular area of his or her body. Magnetic resonance imaging (MRI) is a technique for imaging portions of the body of the patient for purposes of medical diagnosis. During an MRI procedure, the patient is exposed to magnetic and radio frequency (RF) fields to obtain images of a portion of the body. In particular, the patient is exposed to a strong static (i.e., non-varying) magnetic field that is typically always present around the MRI device whether or not a procedure is in progress. In the presence of the strong static magnetic field, a number of gradient (i.e., time-varying) magnetic fields and RF fields are applied during the MRI procedure to obtain the desired images. The magnitude, frequency or other characteristic of the various fields applied during the MRI procedure may vary based on the type of device producing the fields or the type of scan being performed.

Exposure of the implantable medical system to the various fields generated by the MRI device may result in undesirable operation of the implantable medical system. In some instances, the gradient magnetic fields or the RF fields may induce a current or voltage on the leads of the implantable medical system. The current or voltage induced on the leads may interfere with the ability of the IMD to properly sense cardiac signals of the heart of the patient. For example, current or voltage induced on the lead by the gradient magnetic or RF fields may cause the IMD to incorrectly sense a cardiac signal when one is not present or to fail to sense a cardiac signal when one is present. Such interference may result in the IMD delivering therapy when it is not desired or withholding therapy when it is desired.

SUMMARY

In general, this disclosure relates to techniques to improve sensing by an IMD during exposure to an interfering signal. The IMD may adjust one or more sensing parameters or may utilize different sensing components of a sensing module of the IMD prior to or immediately subsequent to entering an environment having an external source that generates the interfering signal. The IMD may, for example, adjust a sampling frequency, resolution, input range, gain, bandwidth, filtering parameters, or a combination of these or other sensing parameters of the sensing module. These adjustments enable the sensing module to obtain a more detailed representation of the sensed signals, including the noise components of the sensed signals caused by the interfering signal. Without having an adequate representation of the noise components of the sensed signal, it is difficult to separate the noise components of the sensed signal from the cardiac electrical signal.

By increasing the sampling frequency and/or resolution of the sensing module, the sensing module may obtain a more detailed digital representation of the sensed signal, including non-linearities, spikes, or other shapes of the sensed signal. As another example, the IMD may increase the input range and/or decrease the gain of the sensing module to reduce the likelihood of clipping of the sensed signal to again obtain a more detailed representation of the sensed signal. As a further example, the IMD may increase the bandwidth and/or decrease the filtering of the sensing module to capture the spectral components of the sensed signal that are outside the usual frequency bands of interest to obtain a more accurate representation of the sensed signal. The IMD may subsequently perform any of a number of signal processing techniques to the enhanced sensed signal to reduce the distortion induced on the cardiac electrical signal by the interfering signal.

In one example, this disclosure is directed to an implantable medical device comprising a sensing module to sense electrical signals and a processor. The processor receives an input associated with the presence of an environment having an external source that generates an interfering signal and adjusts a sensing configuration of the sensing module to reduce the likelihood of clipping of sensed signals that include noise caused by the interfering signal. The sensing module senses signals using the adjusted sensing configuration while in the presence of the environment having the external source that generates the interfering signal.

In another example, this disclosure is directed to a method comprising receiving an input associated with the presence of an environment having an external source that generates an interfering signal, adjusting a sensing configuration of a sensing module of an implantable medical device to reduce the likelihood of clipping of sensed signals that include noise caused by the interfering signal, and sensing signals using the adjusted sensing configuration while in the presence of the environment having the external source that generates the interfering signal.

In a further example, this disclosure is directed to a computer-readable medium comprising instructions that, when executed by a processor, cause the processor to receive an input associated with the presence of an environment having an external source that generates an interfering signal, adjust a sensing configuration of a sensing module of an implantable medical device to reduce the likelihood of clipping of sensed signals that include noise caused by the interfering signal, and sense signals using the adjusted sensing configuration while in the presence of the environment having the external source that generates the interfering signal.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
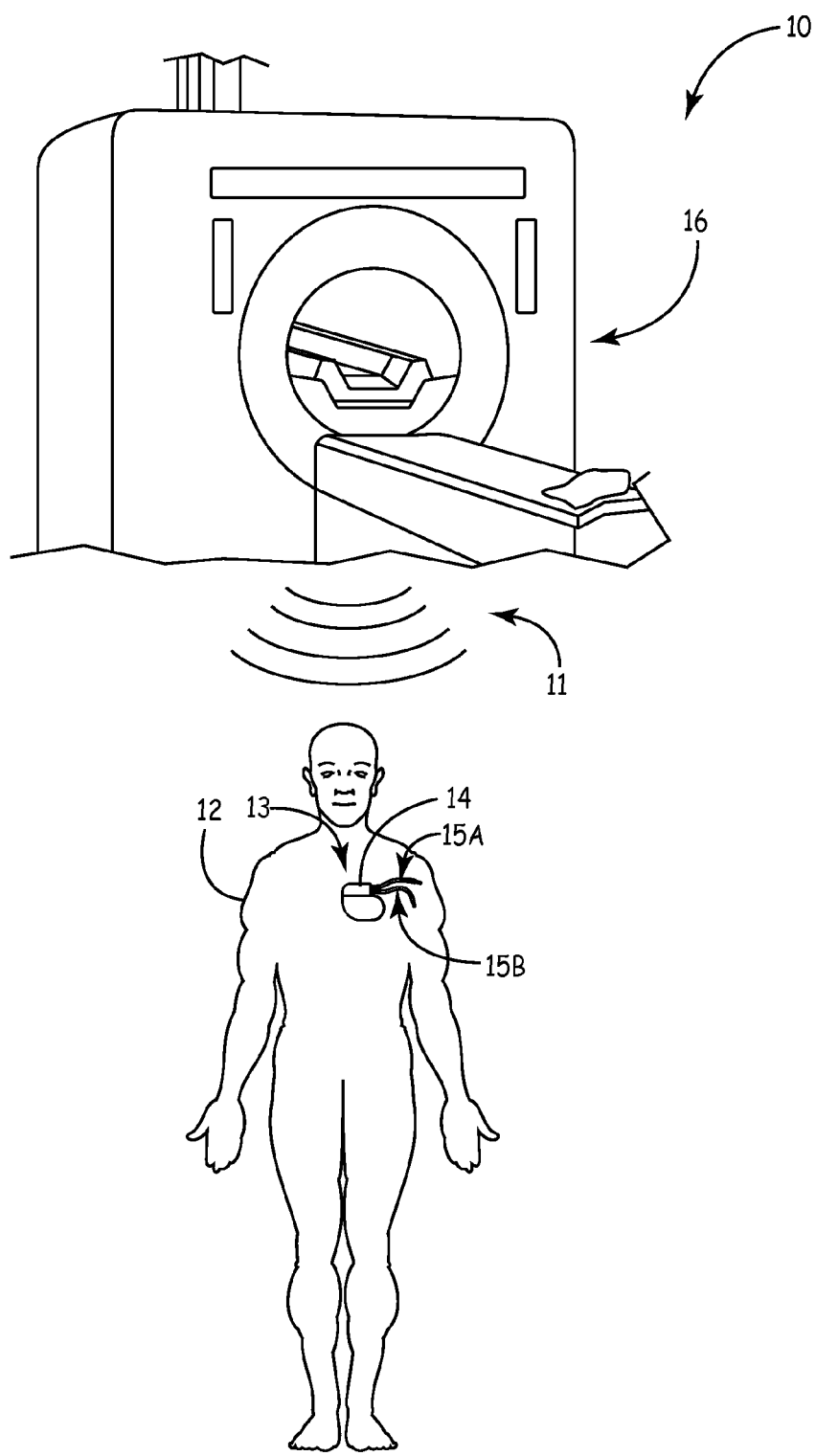
FIG. 1 is a conceptual diagram illustrating an environment in which an implantable medical system is exposed to an interfering signal from an external source.

FIG. 1 is a conceptual diagram illustrating an environment 10 in which an implantable medical system 13 is exposed to an interfering signal 11 from an external source. Implantable medical system 13 of FIG. 1 includes an implantable medical device (IMD) 14 and one or more leads (e.g., leads 15A and 15B, collectively "leads 15") implanted within patient 12. IMD 14 and leads 15 are adapted to provide therapy to and/or to monitor a physiological condition of patient 12. The techniques, however, are not limited to devices implanted within patient 12. For example, the techniques may be used in conjunction with an external medical system that is adversely affected by interfering signal 11.

Environment 10 includes an external energy source 16 that generates interfering signal 11 to which implantable system 13 is exposed. In the example illustrated in FIG. 1, the external energy source is an MRI device 16. Although the techniques of this disclosure are described with respect to interfering signal 11 generated by MRI device 16, the techniques may be used to control operation of IMD 14 within environments in which other types of interfering signals are present. For example, IMD 14 may operate in accordance with the techniques of this disclosure in environments in which interfering signal 11 is generated by other sources, such as electrocautery devices, diathermy devices, ablation devices, radiation therapy devices, electrical therapy devices, magnetic therapy devices, radio frequency identification (RFID) readers, or any other environment with devices that radiate energy to produce magnetic, electromagnetic, electric or other disruptive energy fields.

MRI device 16 uses magnetic and RF fields to produce images of body structures for diagnosing injuries, diseases and/or disorders. In particular, MRI device 16 generates a static magnetic field, gradient magnetic fields and/or RF fields. The static magnetic field is a non-varying magnetic field that is typically always present around MRI device 16 whether or not an MRI scan is in progress. Gradient magnetic fields are time-varying magnetic fields that are typically only present while the MRI scan is in progress. RF fields are pulsed RF fields that are also typically only present while the MRI scan is in progress. The magnitude, frequency or other characteristic of interfering signal 11 may vary based on the type of MRI device producing the field. A 1.5 Tesla MRI device, for example, generates a static magnetic field at approximately 15,000 Gauss, generates gradient magnetic fields up to approximately 45 mT/m at 200 T/m/s, and generates RF pulses at approximately 64 MHz.

Some or all of the various types of fields produced by MRI device 16 may interfere with the operation of IMD 14. In other words, one or more of the various types of fields produced by MRI device 16 may make up interfering signal 11. For example, the gradient magnetic fields or RF fields produced by MRI device 16 may interfere with sensing by IMD 14. In particular, the gradient magnetic fields and RF fields produced by MRI device 16 may induce currents or voltages on implantable leads 15 coupled to IMD 14. In some instances, IMD 14 inappropriately detects the induced current or voltage on leads 15 as physiological signals, which may in turn cause IMD 14 to deliver undesired therapy or withhold desired therapy. In other instances, the induced current or voltage on leads 15 result in IMD 14 not detecting physiological signals that are actually present, which may again result in IMD 14 delivering undesired therapy or withholding desired therapy.

This disclosure describes techniques to improve sensing during exposure to interfering signal 11. IMD 14 may be configured into an MRI-compatible operating mode prior to or immediately subsequent to entering environment 10. The MRI-compatible operating mode may include changing the operating parameters of sensing components or utilizing different sensing components of IMD 14 to provide enhanced sampling of sensed signals. The MRI-compatible operating mode may, for example, adjust a sampling frequency, resolution, input range, gain, bandwidth, filtering parameters, or a combination of these or other sensing parameters of the sensing module to obtain more details about components of the sensed signal that are outside the usual frequency or amplitude ranges of interest. In other words, the adjustments to the sensing module enable IMD 14 to obtain a more detailed representation of the sensed signals, including the noise components of the sensed signals caused by interfering signal 11. With a more accurate representation of the noise components of the sensed signal, IMD may more easily perform signal processing techniques to the enhanced sensed signal to reduce the distortion induced on the cardiac electrical signal by the interfering signal.

IMD 14 may receive an input associated with the presence of environment 10 having an external source that generates interfering signal 11 and adjust the sensing configuration of the sensing module in response to the input. IMD 14 may, for example, be automatically configured into the MRI-compatible operating mode in response to detecting one or more conditions indicative of the presence of MRI device 16, e.g., existence of a strong magnetic field detected by a Hall sensor or other magnetic sensor. In this example, the detection of the one or more conditions indicative of the presence of MRI device 16 is the input associated with the presence of environment 10. In other instances, IMD 14 is manually programmed into the MRI-compatible operating mode prior to entering environment 10. For example, an external device (not illustrated) may wirelessly communicate with IMD 14 to send one or more commands that cause IMD 14 to transition to the MRI-compatible operating mode. In this example, the one or more commands received via wireless communication are the input associated with the presence of environment 10.

Although the techniques of this disclosure are described in the context of environment 10 including an MRI device 16 as the external source, the techniques may be used in other environments in which the standard sampling configuration does not allow for accurate interpretation of cardiac electrical signals due to interfering signals, including but not limited environments during electrocautery procedures, diathermy procedures, ablation procedures, radiation therapy procedures, electrical therapy procedures, and magnetic therapy procedures.

Figure 2:
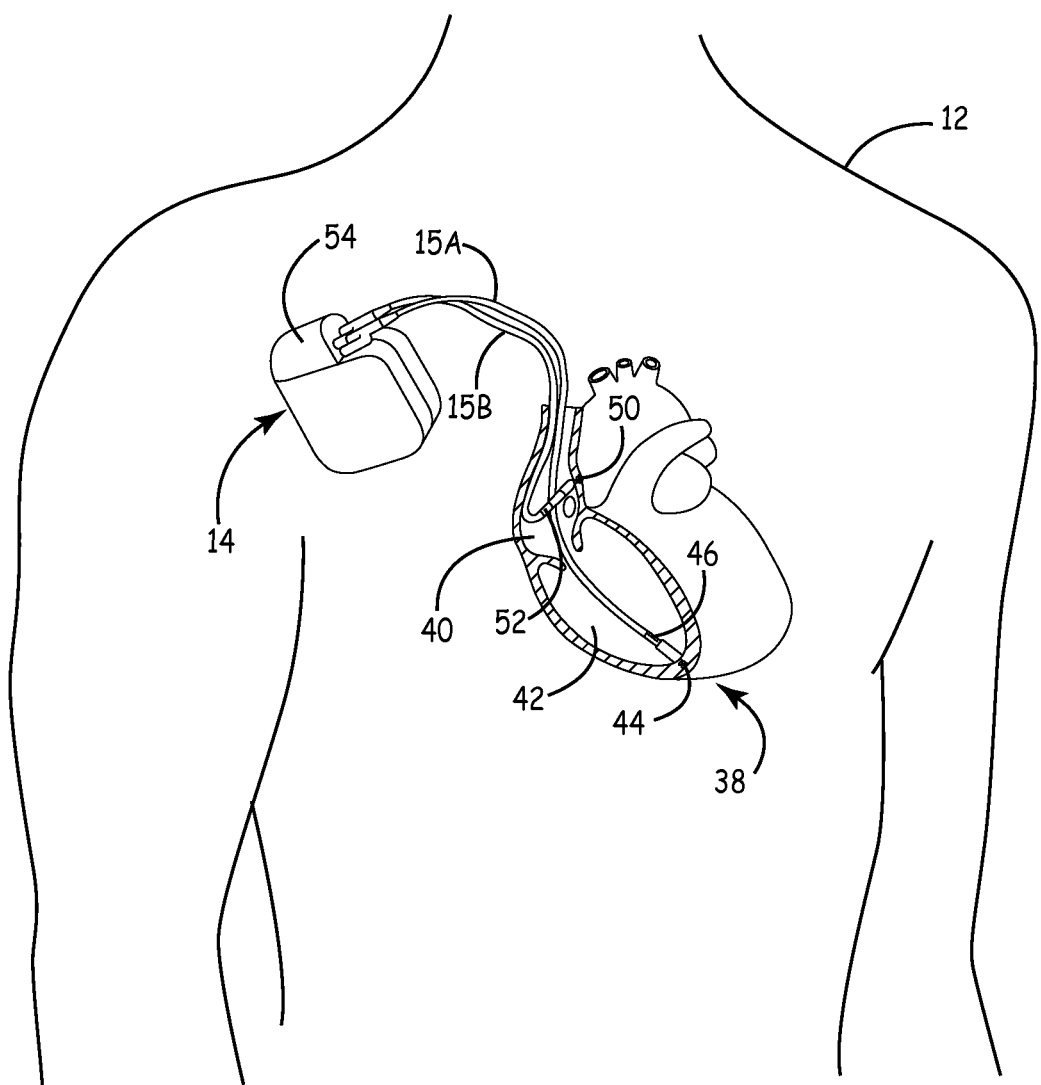
FIG. 2 is a conceptual diagram illustrating the implantable medical system of FIG. 1 in more detail.

FIG. 2 is a conceptual diagram illustrating implantable medical system 13 in more detail. Implantable medical system 13 includes an IMD 14 and leads 15A and 15B that extend from IMD 14. In the example illustrated in FIG. 2, IMD 14 is an implantable cardiac device that senses electrical activity of a heart 38 of patient 12 and provides electrical stimulation therapy to heart 38 of patient 12. The electrical stimulation therapy to heart 38, sometimes referred to as cardiac rhythm management therapy, may include pacing, cardioversion, defibrillation and/or cardiac resynchronization therapy (CRT).

In the illustrated example, lead 15A is a right ventricular (RV) lead that extends through one or more veins (not shown), the superior vena cava (not shown), and right atrium 40, and into right ventricle 42 of heart 38. Lead 15A includes electrodes 44 and 46 located along a distal end of lead 15A. In the illustrated example, lead 15B is right atrial (RA) lead that extends through one or more veins and the superior vena cava, and into the right atrium 40 of heart 38. Lead 15B includes electrodes 50 and 52 located along a distal end of lead 15B.

Electrodes 44 and 50 may take the form of extendable helix tip electrodes mounted retractably within an insulative electrode head (not shown) of respective leads 15. Electrodes 46 and 52 may take the form of ring electrodes. In other embodiments, electrodes 44, 46, 50 and 52 may be other types of electrodes. For example, electrodes 44, 46, 50 and 52 may all be ring electrodes located along the distal end of the associated leads 15. Additionally, either or both of leads 15 may include more than two electrodes or only a single electrode.

Each of the electrodes 44, 46, 50 and 52 may be electrically coupled to a respective conductor within the body of its associated lead 15. The respective conductors may extend from the distal end of the lead to the proximal end of the lead and couple to circuitry of IMD 14. For example, leads 15 may be electrically coupled to a stimulation module, a sensing module, or other modules of IMD 14 via connector block 54. In some examples, the proximal ends of leads 15 may include electrical contacts that electrically couple to respective electrical contacts within connector block 54. In addition, in some examples, leads 15 may be mechanically coupled to connector block 54 with the aid of set screws, connection pins or another suitable mechanical coupling mechanism.

Electrodes 44, 46, 50 and 52 may be used to sense cardiac electrical signals attendant to the depolarization and repolarization of heart 38. The cardiac electrical signals are conducted to IMD 14 via one or more conductors of respective leads 15. IMD 14 may use any combinations of the electrodes 44, 46, 50, 52 or the housing electrode for unipolar or bipolar sensing. As such, the configurations of electrodes used by IMD 14 for sensing and pacing may be unipolar or bipolar depending on the application. IMD 14 may analyze the sensed signals to monitor a rhythm of heart 38 or detect an abnormal arrhythmia of heart 38, e.g., tachycardia, bradycardia, fibrillation or the like. In some instances, IMD 14 provides electrical stimulation therapy based on the cardiac signals sensed within heart 38. For example, IMD 14 may trigger or inhibit delivery of the electrical stimulation therapy based on the sensed cardiac signals. In other words, the electrical stimulation therapy may be responsive to the sensed events.

As described above with respect to FIG. 1, exposure of IMD 14 to an interfering signal 11 may introduce noise on the signals received by the sensing components of IMD 14. This noise may cause IMD 14 to inappropriately detect cardiac events not actually present (i.e., oversense) or to not detect cardiac events that are actually present (i.e., undersense). In either case, the oversensing or undersensing may cause IMD 14 to deliver undesired therapy or withhold desired therapy.

Configuring IMD 14 to operate in accordance with adjusted sensing capabilities may enhance the representation of the sensed signal and thus allow IMD 14 to more easily reduce, and possibly eliminate, the noise components of the signal using signal processing techniques. As such, IMD 14 may be configured to an MRI-compatible operating mode that includes adjustments to one or more sensing parameters or the utilization of different sensing components prior to or immediately subsequent to entering environment 10 in which the interfering signal 11 is present.

The configuration of implantable medical system 13 illustrated in FIGS. 1 and 2 is merely an example. In other examples, implantable medical system 13 may include more or fewer leads extending from IMD 14. For example, IMD 14 may be coupled to three leads, e.g., a third lead implanted within a left ventricle of heart 38. In another example, IMD 14 may be coupled to a single lead that is implanted within either an atrium or ventricle of heart 38. As such, IMD 14 may be used for single chamber or multi-chamber cardiac rhythm management therapy.

In addition to more or fewer leads, each of the leads may include more or fewer electrodes. In instances in which IMD 14 is used for therapy other than pacing, e.g., defibrillation or cardioversion, the leads may include elongated electrodes, which may, in some instances, take the form of a coil. IMD 14 may deliver defibrillation or cardioversion shocks to heart 38 via any combination of the elongated electrodes and housing electrode. As another example, implantable medical system 13 may include leads with a plurality of ring electrodes, e.g., as used in some implantable neurostimulators.

The techniques of this disclosure are described in the context of cardiac rhythm management therapy for purposes of illustration. The techniques of this disclosure, however, may be used to operate an IMD that provides other types of electrical stimulation therapy. For example, the IMD may be a device that provides electrical stimulation to a tissue site of patient 12 proximate a muscle, organ or nerve, such as a tissue proximate a vagus nerve, spinal cord, brain, stomach, pelvic floor or the like. As such, description of these techniques in the context of cardiac rhythm management therapy should not be limiting of the techniques as broadly described in this disclosure.

Figure 3:
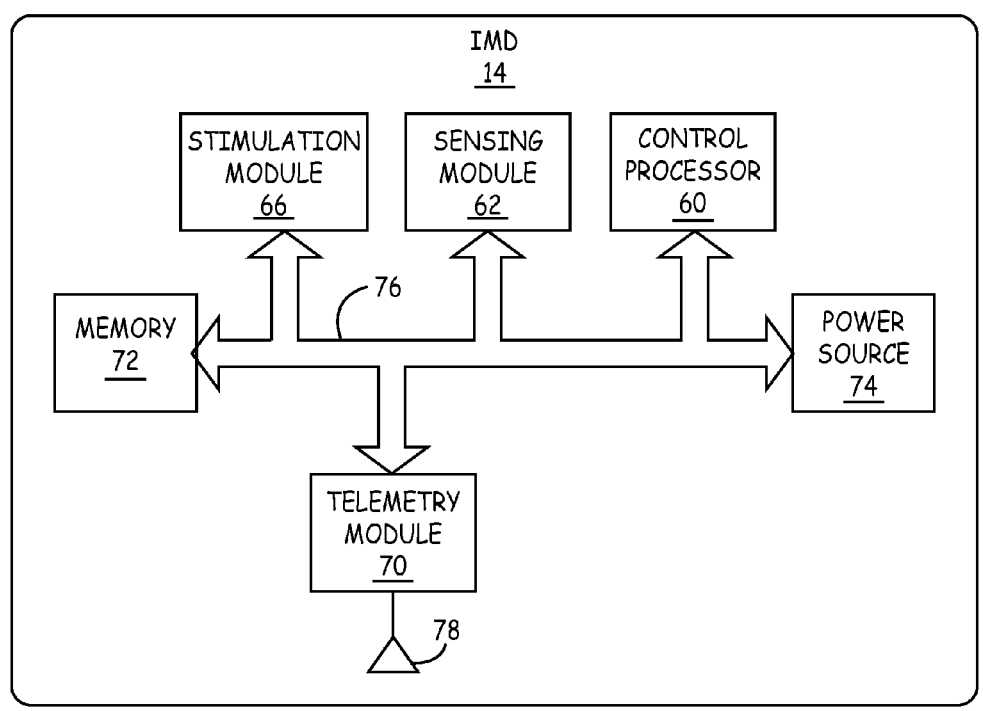
FIG. 3 is a functional block diagram of an example configuration of components of an IMD of the implantable medical system.

FIG. 3 is a functional block diagram of an example configuration of components of IMD 14. In the example illustrated by FIG. 3, IMD 14 includes a control processor 60, sensing module 62, stimulation module 66, telemetry module 70, memory 72 and power source 74. The components of IMD 14 are illustrated as being interconnected by a data bus 76, but may be connected by one or more direct electrical connections in addition to or instead of data bus 76.

One or more electrodes 44, 46, 50, or 52 (or the housing electrode) senses electrical signals attendant to the depolarization and repolarization of heart 38. In this manner, the electrodes may be viewed as sensors. Thus, the term "sensor" as used herein may include an electrode. The electrical signals sensed by electrodes 44, 46, 50, or 52 are conducted to sensing module 62 of via one or more conductors of leads 15. In other instances, leads 15 may include one or more sensors dedicated for sensing. In further examples, sensing module 62 is coupled to one or more sensors that are not included on leads 15, e.g., via a wired or wireless coupling. Other types of sensor besides electrodes may include, but are not limited to, pressure sensors, accelerometers, flow sensors, blood chemistry sensors, activity sensors or other type of physiological sensor.

Sensing module 62 includes sensing components used to process signals received from the one or more sensors. The components of sensing module 62 may be analog components, digital components or a combination thereof. Sensing module 62 may include multiple sensing channels each having associated sensing components. Each sensing channel may, for example, include one or more sense amplifiers, filters, rectifiers, threshold detectors, analog-to-digital converters (ADCs) or the like. Some sensing channels may convert the sensed signals to digital form and provide the digital signals to processor 60 for processing or analysis. For example, sensing module 62 may amplify signals from the sensing electrodes and convert the amplified signals to multi-bit digital signals by an ADC. Processor 60 may store the digitized versions of signals as EGMs in memory 72. Other sensing channels may compare processed signals to a threshold to detect the existence of P- or R-waves and indicate the existence of the P- or R-waves to processor 60.

Exposure of IMD 14 to an interfering signal 11 may introduce noise on the cardiac signals received by sensing module 62 of IMD 14. The noise on the sensed signals may result in sensed signals that are incoherent. Additionally, the noise on the sensed signals may cause IMD 14 to inappropriately detect cardiac events not actually present (i.e., oversense) or to not detect cardiac events that are actually present (i.e., undersense). The oversensing or undersensing may cause IMD 14 to deliver undesired therapy or withhold desired therapy.

The spectral components of the noise induced by interfering signal 11 on the sensed signal typically differs in frequency and amplitude relative to the spectral components of cardiac electrical signals. Filtering can reduce the effects of the induced noise, but the filtering may be inadequate for accurately interpreting cardiac electrical signals due to the potentially large amplitude of the noise and the energy components of the noise that overlap with and extend beyond the frequency band of the cardiac electrical signals. To allow for more effective reduction of the noise induced by interfering signal 11, it may be advantageous to reduce the amount of information that is lost by temporarily implementing a sampling configuration capable of more accurately recording the induced noise, without affecting the integrity of the cardiac electrical signals.

In accordance with the techniques of this disclosure, processor 60 may change the sensing configuration of sensing module 62 prior to or immediately subsequent to entering environment 10 to improve the sensing capability of IMD 14 and thus better distinguish between noise induced by interfering signal 11 and the cardiac electrical signals. Processor 60 may receive an input associated with the presence of environment 10 having an external source that generates interfering signal 11 and adjust the sensing configuration of sensing module 62 in response to the input. The aspects of the sensing configuration of sensing module 62 that may be adjusted include a sampling frequency, resolution, input range, gain, bandwidth, filtering parameters, or a combination thereof. By increasing the sampling frequency and/or resolution, for example, sensing module 62 may obtain a more detailed digital representation of the sensed signal (noise+cardiac electrical signal), including non-linearities, spikes, or other shapes of the sensed signal. Without having an adequate representation of the sensed signal, it may be difficult to separate the noise signal from the cardiac electrical signal. As another example, processor 60 may increase the input range and/or decrease the gain of sensing module 62 to reduce the likelihood of clipping of the sensed signal to again obtain a more detailed representation of the sensed signal. As a further example, processor 60 may increase the bandwidth and/or decrease the filtering of sensing module 62 to capture the spectral components of the sensed signal that are outside the usual amplitude or frequency bands of interest, thus obtaining a more detailed sensed signal.

Processor 60 may implement these adjustments alone or in combination. In other words, processor 60 may adjust only a single sensing parameter of sensing module 62 or a combination of sensing parameters of sensing module 62. In instances in which processor 60 adjusts more than one sensing parameter, processor 60 may adjust the sensing parameters concurrently and independently. In other words, the adjustments of the various parameters are not dependent on one another. In another example, the adjustment of one parameter may be dependent on the signal sensed using a previously adjusted parameter. For example, processor 60 may adjust the sampling frequency to obtain a more detailed version of the sensed signal and, based on the more detailed sensed signal, processor 60 may further adjust the gain, input range, resolution, bandwidth, and/or filtering parameters of sensing module 62. In this manner, adjustment of some of the parameters may be made based on analysis of the sensed signal using a previously adjusted parameter.

Processor 60 may employ digital signal analysis techniques to more effectively distinguish between the induced noise and cardiac electrical signals. Processor 60 may perform additional filtering or subtraction to reduce the amount of noise within the sensed signal. Alternatively, processor 60 may perform one or more transform techniques (e.g., Fast Fourier Transform (FFT), wavelet transform, or other transform technique) to distinguish between the induced noise and the cardiac electrical signals. Processor 60 may also obtain an independent noise signal representative of the noise without the cardiac electrical signal and adaptively filter the noise signal from the sensed signal to obtain the cardiac electrical signal. Processor 60 may, for example, obtain the independent noise signal using a telemetry antenna and associated telemetry components (e.g., amplifier, ADC, etc). As another example, processor 60 may obtain the independent noise signal from a noise detector within IMD 14 or otherwise coupled to IMD 14. As a further example, processor may obtain the independent noise signal from a conductor within the lead that is associated with a non-sensing electrode.

Processor 60 may control stimulation module 66 to provide electrical stimulation therapy based on the cardiac electrical signals extracted from the sensed signals by processor 60. When IMD 14 is configured to generate and deliver therapy to heart 38, control processor 60 controls stimulation module 66 to deliver electrical stimulation therapy to heart 38 via one or more of electrodes 44, 46, 50, 52 and/or the housing electrode. Stimulation module 66 is electrically coupled to electrodes 44, 46, 50 and 52, e.g., via conductors of the respective leads 15, or, in the case of the housing electrode, via an electrical conductor disposed within the housing of IMD 14.

Control processor 60 controls stimulation module 66 to generate and deliver electrical pacing pulses with the amplitudes, pulse widths, rates, electrode combinations or electrode polarities specified by a selected therapy program. For example, electrical stimulation module 66 may deliver bipolar pacing pulses via ring electrodes 46 and 52 and respective corresponding helical tip electrodes 44 and 50 of leads 15. To this end, stimulation module 66 may include a pulse generator or other components needed to generate electrical stimulation signals. Stimulation module 66 may deliver one or more of these types of stimulation in the form of other signals besides pulses or shocks, such as sine waves, square waves, or other substantially continuous signals. In addition to pacing pulses, stimulation module 66 may, in some instances, deliver other types of electrical therapy, such as defibrillation and/or cardioversion therapy.

Control processor 60 may include any one or more of a microprocessor, a controller, a digital signal processor (DSP), an application specific integrated circuit (ASIC), a field-programmable gate array (FPGA), or equivalent discrete or integrated circuitry, including analog circuitry, digital circuitry, or logic circuitry. The functions attributed to control processor 60 herein may be embodied as software, firmware, hardware or any combination thereof.

Memory 72 may include computer-readable instructions that, when executed by control processor 60 or other component of IMD 14, cause one or more components of IMD 14 to perform various functions attributed to those components in this disclosure. Memory 72 may include any volatile, non-volatile, magnetic, optical, or electrical media, such as a random access memory (RAM), read-only memory (ROM), non-volatile RAM (NVRAM), static non-volatile RAM (SRAM), electrically-erasable programmable ROM (EEPROM), flash memory, or any other computer-readable storage media.

The various components of IMD 14 are coupled to power source 74, which may include a rechargeable or non-rechargeable battery. A non-rechargeable battery may be capable of holding a charge for several years, while a rechargeable battery may be inductively charged from an external device, e.g., on a daily or weekly basis. Power source 74 also may include power supply circuitry for providing regulated voltages and/or current levels to power the various components of IMD 14.

Under the control of processor 60, telemetry module 70 may receive downlink telemetry from and send uplink telemetry to programming device 18 with the aid of an antenna 78, which may be internal and/or external to IMD 14. As described above, for example, telemetry module 70 may receive commands from a programmer indicating that IMD 14 should transition to the MRI-compatible operating mode. Telemetry module 70 includes any suitable hardware, firmware, software or any combination thereof for communicating with another device, such as programming device 18. For example, telemetry module 70 may include appropriate modulation, demodulation, encoding, decoding, frequency conversion, filtering, and amplifier components for transmission and reception of data.

The various modules of IMD 14 may include one or more processors, such as one or more microprocessors, DSPs, ASICs, FPGAs, programmable logic circuitry, or the like, that may perform various functions and operations, such as those described herein. Although illustrated in FIG. 3 as separate modules, the functionality attributed to the modules may be performed by common hardware, firmware or software components. For example, one or more functions attributed to sensing module 62, such as digital filtering or threshold detection, may be performed by the same processor that functions as control processor 60.

Figure 4:
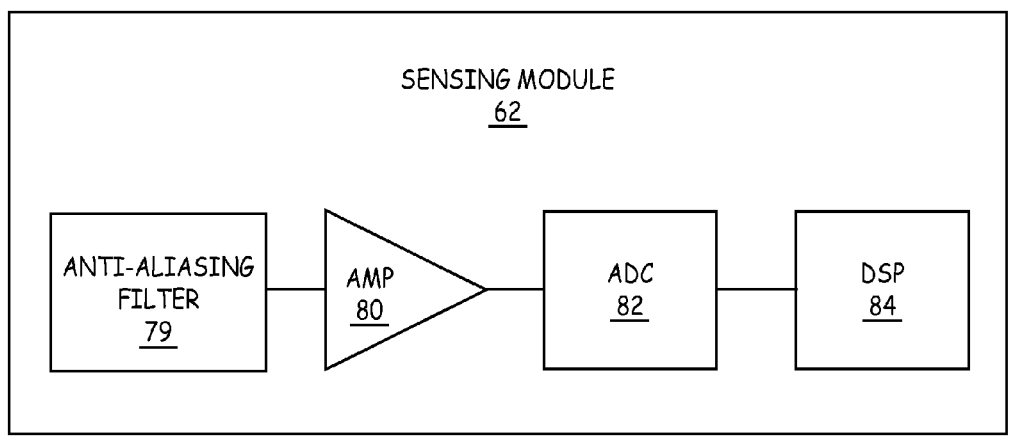
FIG. 4 is a functional block diagram illustrating components of an example sensing module of an IMD.

FIG. 4 is a functional block diagram illustrating components of an example sensing module 62 in further detail. Sensing module 62 includes an anti-aliasing filter 79, amplifier 80, ADC 82, and digital signal processor (DSP) 84. Sensing module 62 may include other components in addition to those illustrated in FIG. 4, such as a rectifier, threshold detector or other components to process the sensed signal.

The components illustrated in FIG. 4 may form a first sensing channel of sensing module 62. The sensing channel processes the sensed signal and provides the processor signal or a result obtained from processing the sensed signal (e.g., existence of a P- or R-wave) to processor 60. The first sensing channel may, for example, process signals sensed by electrodes 44 and 46 of lead 15A. As described above, however, sensing module 62 may have more than one sensing channel, such as a sensing channel for an atrial electrical signal and a sensing channel for a ventricular electrical signal. In this case, sensing module 62 may include additional components forming additional sensing channels. The multiple sensing channels may share one or more of components or may have their own separate components.

Sensing module 62 receives a signal sensed by one or more electrodes 44, 46, 50 and 52, filters, amplifies, and converts the signal to a digital format for subsequent signal processing. The signal received by sensing module 62 includes cardiac electrical signals and any noise signal induced on leads 15, including noise signals induced by interfering signal 11. Sensing module 62 may have one or more adjustable parameters, such as an adjustable sampling frequency, resolution, gain, input range, bandwidth, and/or filtering parameters. Sensing module 62 may also have one or more selectable components. In some instances all of these parameters or components are adjustable or selectable, while in other embodiments only one or a portion of these parameters or components are adjustable or selectable. As described above, processor 60 may adjust one or more of the parameters or may select one or more components of sensing module 62 to provide enhanced sensing when exposed to interfering signal 11.

For example, processor 60 may adjust a gain of amplifier 80. The gain of an amplifier is the ratio of output voltage to input voltage. During typical operation (e.g., when not exposed to interfering signal 11), the gain of the amplifier typically ranges from several tens to several hundreds. Such a gain is acceptable for amplifying cardiac electrical signals.

However, the noise signals induced on the lead may have amplitudes that are larger than the cardiac electrical signals. In this case, amplifying the sensed signals (i.e., cardiac electrical activity+noise) using the conventional gain may result in amplifier 80 saturating or ADC 82 clipping portions of the sensed signal. Saturation or clipping is a form of distortion that truncates a signal once it exceeds a threshold of amplifier 80 or ADC 82. When the signal reaches the threshold, amplifier 80 or ADC 82 outputs its largest amplitude regardless of the actual amplitude of the signal. Thus, the clipping distorts the sensed signal by removing details about the portions of the sensed signal above the threshold.

As described above, the more detail obtained regarding the characteristics of the sensed signal, the easier it is for control processor 60 to separate the portion of the sensed signal attributed to the interfering signal from the portion of the signal attributed to the cardiac electrical signal. Therefore, processor 60 may decrease the gain of amplifier 80 (e.g., by changing the resistance of a component(s) of the amplifier or by programming the gain via software) prior to or immediately subsequent to entering environment 10 to reduce the likelihood of clipping of the sensed signal. Processor 60 may, for example, decrease the gain by a certain factor (e.g., by 50%) or dynamically adjust the gain (e.g., using a signal limiter, which will allow signals below a certain threshold to pass unaffected while attenuating signals above a certain threshold). By reducing the amount of clipping that occurs, sensing module 62 obtains more detail regarding the characteristics of the sensed signal (e.g., amplitude, shape, etc).

A limited input range of ADC 82 may have a similar effect on the sensed signal, i.e., the input range of ADC 82 may cause clipping of the sensed signal when the sensed signal includes the interfering signal 11. The input range of an ADC 82 is the range of values it is capable of converting. During typical operation (e.g., when not exposed to interfering signal 11), the input range of ADC 82 may be between 0 V and approximately 1 V. Such an input range is acceptable amplifying cardiac electrical signals.

However, the amplified noise signals induced on leads 15 by interference signal 11 may have amplitudes that exceed the input range of ADC 82. In this case, ADC 82 may clip portions of the sensed signal. Therefore, processor 60 may increase the input range of ADC 82 (e.g., by increasing the reference voltage supplied to ADC 82) prior to or immediately subsequent to entering environment 10 to reduce the likelihood of clipping of the sensed signal. Processor 60 may, for example, increase the input range by a certain factor (e.g., 100%) or dynamically adjust the input range (e.g., based on the amplitude of the signals being converted). In other instances, sensing module 62 may include a plurality of ADCs, and processor 60 may select a higher resolution ADC in order to more effectively process the signals. By reducing the amount of clipping that occurs, sensing module 62 obtains more detail regarding the characteristics of the sensed signal (e.g., amplitude, shape, etc).

In another example, processor 60 may adjust the bandwidth of sensing module 62. The bandwidth is the range of signal frequencies that sensing module 62 can process. Generally, a bandwidth of sensing module 62 is based on the frequency of the signal of interest, e.g., the cardiac electrical signals. Sensing module 62 may, for example, generally operate with a baseband bandwidth of approximately 100 Hz or less during typical operation of IMD 14 (e.g., when not exposed to interfering signal 11).

As described above, however, noise induced on the sensed signal by interfering signal 11 has frequencies outside of the typical frequencies of interest. Some of the frequency components of the portion of the sensed signal corresponding to the noise may be removed from the sensed signal because they are outside of the bandwidth of sensing module 62. As a result, some of the characteristics of the sensed signal including the distortions attributed to noise may be removed. To obtain a more detailed representation of the sensed signal including the noise induced by interfering signal 11, processor 60 may increase the bandwidth. For example, the cutoff frequency of anti-aliasing filter 79 (the input stage of sensing module 62) may be increased. Processor 60 may, for example, increase the baseband bandwidth of sensing module 62 to approximately 1000 Hz. In other instances, processor 60 may increase the bandwidth of sensing module 62 by decreasing the gain of amplifier 80 (gain-bandwidth product). In yet other instances, sensing module 62 may include a plurality of amplifiers and processor 60 may select a higher bandwidth amplifier in order to more effectively process the signals.

ADC 82 of sensing module 62 samples the amplified signal at a particular sampling frequency to convert the analog signal to a plurality of digital samples that provide a digital representation of the analog signal. ADC 82 may sample the amplified signal between approximately 200 and 300 Hertz (Hz) during typical operation (e.g., when not exposed to interfering signal 11) to obtain a digital representation of the cardiac electrical activity. However, such a sampling frequency may not be sufficient when the sensed signal includes distortion caused by interfering signal 11. For example, non-linearities, spikes, or other details of the shape of the sensed signal may be lost when sampling at the typical sampling rate. Therefore, processor 60 may increase the sampling frequency of ADC 82 prior to or immediately subsequent to entering environment 10 to capture more detail about the noise signal. For example, processor 60 may provide a faster clock used by ADC 82 to sample the analog signal. Processor 60 may, in one instance, increase the sampling frequency of ADC 82 to be larger than approximately 1 kHz (e.g., 4 or 5 kHz) to provide enhanced sensing during the exposure to interfering signal 11.

Digital signal processor 84 of sensing module 62 filters the sensed signal to remove frequency components of the sensed signal that are not of interest. In the example illustrated in FIG. 4, digital signal processor 84 is located after ADC 82 and thus would comprise a digital filter. Digital signal processor 84 may filter the sensed signal to block frequencies that do not correspond with the frequencies of interest. Digital signal processor 84 may be a band pass filter that passes signals that have a frequency between approximately 20 Hz and 80 Hz, while blocking all other signals. When the sensed signal includes distortion caused by interfering signal 11, however, the filter may block portions of the signal attributed to interfering signal 11. Therefore, processor 60 may decrease the filtering, e.g., by adjusting the pass band of digital signal processor 84 such that frequencies associated with interfering signal 11 are passed by digital signal processor 84. Processor 60 may, in one instance, increase the pass band of digital signal processor 84 to include frequencies up to hundreds or thousands of Hz to provide enhanced sensing during the exposure to interfering signal 11. Processor 60 may, in another instance, not perform any digital filtering until after the noise signal has been reduced via other signal processing routines.

As described above, processor 60 may implement these adjustments alone or in combination. Processor 60 also analyzes the enhanced sensed signal obtained by sensing module 62 to more effectively distinguish between the induced noise and cardiac electrical signals.

Figure 5:
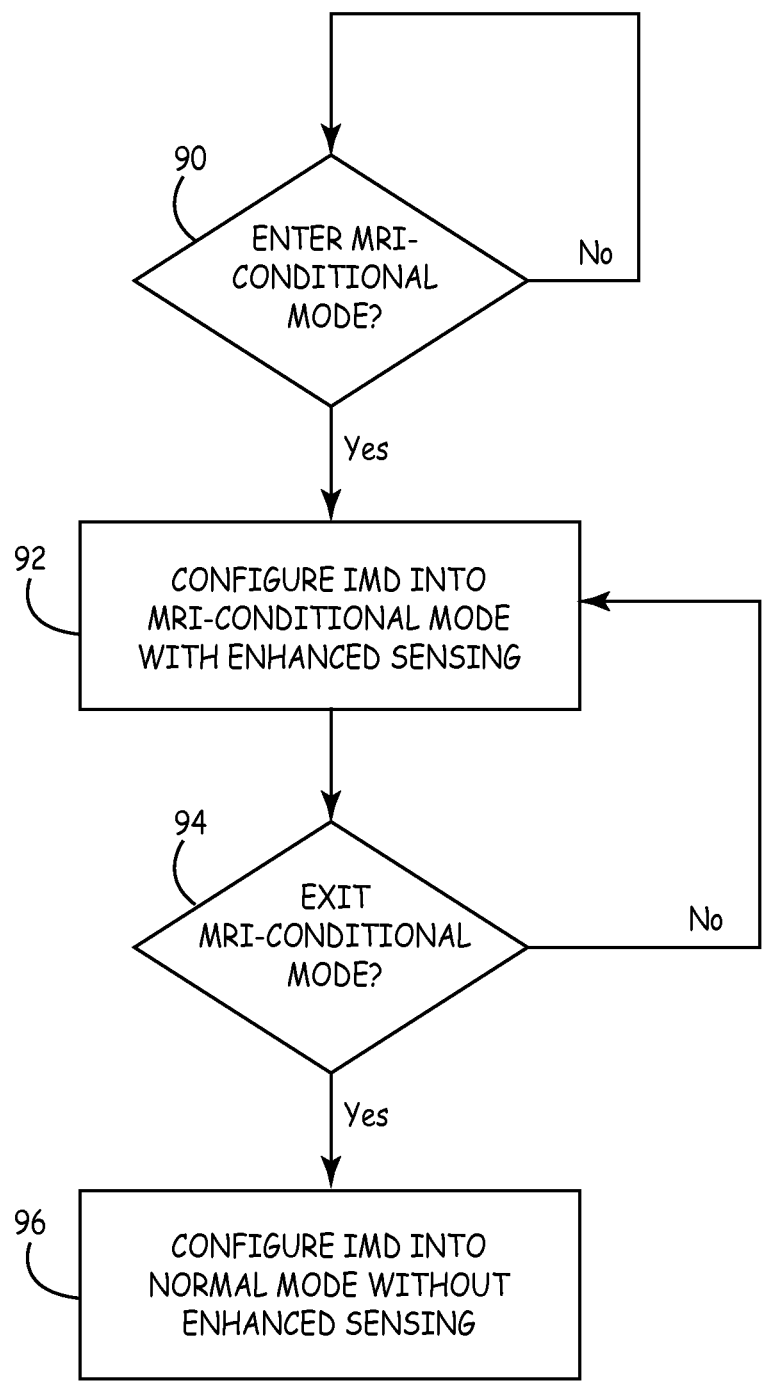
FIG. 5 is a flow diagram illustrating example operation of an IMD adjusting sensing parameters in accordance with the techniques of this disclosure.

FIG. 5 is a flow diagram illustrating example operation of IMD 14 adjusting sensing parameters in accordance with the techniques of this disclosure. Processor 60 initially determines whether to configure IMD 14 into the MRI-compatible mode (block 90). Processor 60 may receive an input associated with the presence of an environment having an external source that generates an interfering signal to determine whether to configure IMD 14 into the MRI-conditional mode. In one example, processor 60 may determine that the MRI-compatible mode needs to be configured in response to detecting one or more conditions indicative of the presence of MRI device 16, e.g., existence of a strong magnetic field detected by a Hall sensor or other magnetic sensor. In this example, the detection of the one or more conditions indicative of the presence of MRI device 16 is the input associated with the presence of environment 10. In another example, IMD 14 may determine that the MRI-compatible mode needs to be configured in response to receiving a command from an external device, e.g. via wirelessly telemetry. In this example, the one or more commands received via wireless communication are the input associated with the presence of environment 10.

In response to determining that the MRI-compatible mode needs to be configured ("Yes" branch of block 90), processor 60 configures IMD 14 into the MRI-compatible operating mode that includes enhanced sensing (block 92). As described in detail above, the MRI-compatible operating mode may include changes to the operating parameters of sensing module 62 or utilizing different sensing components of sensing module 62 to provide the enhanced sensing. The aspects of the sampling configuration of sensing module 62 that may be adjusted include a sampling frequency, resolution, input range, gain, bandwidth, filtering parameters, or a combination thereof. Example adjustments are described above in detail with respect to FIG. 4. Processor 60 may implement these adjustments alone or in combination. Additionally, as described above with respect to FIG. 3, processor 60 may employ digital signal analysis techniques on the enhanced sensed signals to more effectively distinguish between the induced noise and cardiac electrical signals.

Processor 60 determines whether to continue operating in the MRI-conditional operating mode (block 94). Processor 60 may, for example, continue to monitor for a strong static magnetic field and continue to operate IMD 14 in the MRI-conditional operating mode as long as the static magnetic field is detected. As another example, processor 60 may maintain a timer that tracks the amount of time that has elapsed since entering the MRI-conditional mode and exit the MRI-conditional mode when the timer exceeds a threshold. When processor determines to continue operating in the MRI-conditional operating mode ("Yes" branch of block 94), sensing module 62 continues to sense signals of leads 15 using the adjusted sensing parameters or selected components and processor 60 continues to distinguish the induced noise from the cardiac electrical signals.

When processor determines to not continue operating in the MRI-conditional operating mode ("No" branch of block 94), processor 60 reconfigures IMD into the normal operating mode (block 96). In the normal operating mode, sensing module 62 begins to sense signals of leads 15 using the original sensing parameters or originally selected components.

The techniques described in this disclosure, including those attributed to one or more components of IMD 14, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, SRAM, EEPROM, flash memory, magnetic data storage media, optical data storage media, or the like. The instructions may be executed to support one or more aspects of the functionality described in this disclosure.

Various examples have been described. However, the temporary implementation of an enhanced sampling configuration may also be applicable in other types of situations or environments in which the standard sampling configuration does not allow for accurate interpretation of cardiac electrical signals. These and other examples are within the scope of the following claims.

The invention claimed is:

1. A method comprising:
  receiving an input associated with a presence of a magnetic resonance imaging (MRI) device that generates an interfering signal;
  adjusting, in response to receiving the input, a sensing configuration of a sensing module of an implantable medical device to reduce a likelihood of clipping of sensed signals that include noise caused by the interfering signal, wherein adjusting the sensing configuration comprises at least one of increasing an amplitude input range of the sensing module and decreasing an amplitude gain of the sensing module; and
  sensing signals using the adjusted sensing configuration while in the presence of the MRI device.

2. The method of claim 1, wherein increasing the input range of the sensing module comprises increasing a reference voltage supplied to an analog to digital converter (ADC).

3. The method of claim 1, wherein increasing the input range of the sensing module comprises one of increasing the input range by a certain factor or dynamically adjusting the input range.

4. The method of claim 1, wherein decreasing the gain of the sensing module comprises decreasing the gain of an amplifier of the sensing module by one of changing a resistance of one or more components of the amplifier or programming the gain via software.

5. The method of claim 1, wherein decreasing the gain comprises one of decreasing the gain by a certain factor or dynamically adjusting the gain.

6. The method of claim 1, further comprising:
  adjusting at least one of a sampling frequency, a resolution, a bandwidth and a filtering parameter of the sensing module.

7. The method of claim 1, further comprising:
  increasing a sampling frequency of the sensing module of the implantable medical device in response to receiving the input associated with the presence of the MRI device; and
  wherein adjusting the sensing configuration comprises at least one of decreasing the gain of the sensing module or increasing the input range of the sensing module based on analysis of signals sensed using the increased sampling frequency.

8. The method of claim 1, further comprising:
  processing the sensed signal to identify a noise characteristic of MRI interference; and
  removing the noise from the sensed signal.

9. The method of claim 1, wherein receiving the input associated with the presence of the MRI device comprises one of:
  detecting one or more conditions indicative of the presence of the MRI device; and
  receiving a telemetry communication configuring the implantable medical device into an MRI-compatible mode.

10. The method of claim 1, further comprising:
  determining that the implantable medical device is no longer in the presence of the MRI device; and reconfiguring, in response to the determination, the sensing configuration of the sensing module to sensing parameters used prior to receiving the input associated with the presence of the MRI device.

11. The method of claim 1, wherein sensing signals using the adjusted sensing configuration while in the presence of the MRI device comprises sensing signals that include noise caused by the interfering signal of the MRI device without clipping an amplitude of the sensed signals.

12. An implantable medical device comprising:
a sensing module to sense electrical signals and having an amplitude input range; and
a processor configured to receive an input associated with a presence of a magnetic resonance imaging (MRI) device that generates an interfering signal and adjust, in response to receiving the input, a sensing configuration of the sensing module by increasing the amplitude input range to reduce a likelihood of clipping of sensed signals that include noise caused by the interfering signal,
wherein the sensing module senses signals using the adjusted sensing configuration while in the presence of the MRI device.

13. The device of claim 12, wherein the sensing module includes an analog to digital converter (ADC) and the processor increases a reference voltage supplied to the ADC to increase the input range of the sensing module.

14. The device of claim 12, wherein the processor increases the input range of the sensing module by a certain factor or dynamically adjusts the input range.

15. The device of claim 12, wherein the processor decreases a gain of the sensing module to reduce the likelihood of clipping of sensed signals that include noise caused by the interfering signal.

16. The device of claim 15, wherein the sensing module includes an amplifier and the processor decreases the gain of the amplifier by one of changing a resistance of one or more components of the amplifier or programming the gain of the amplifier via software.

17. The device of claim 15, wherein the processor decreases the gain by a certain factor or dynamically adjusts the gain.

18. The device of claim 12, wherein the processor is further configured to
adjust at least one of a sampling frequency, a resolution, a bandwidth and a filtering parameter of the sensing module.

19. The device of claim 12, wherein
the processor increases a sampling frequency of the sensing module in response to receiving the input associated with the presence of the MRI device; and
increases the input range of the sensing module to reduce the likelihood of clipping based on analysis of signals sensed using the increased sampling frequency.

20. The device of claim 12, further comprising a digital signal processor to process the sensed signal to identify a noise characteristic of MRI interference and remove the noise from the sensed signal.

21. The device of claim 12, further comprising at least one sensor configured to detect one or more conditions indicative of the presence of the MRI device, wherein the detection of the one or more conditions indicative of the presence of MRI device is the input associated with the presence of the MRI device.

22. The device of claim 12, further comprising a telemetry module configured to receive a command from an external device to enter an MRI-compatible mode, wherein the command to enter the MRI-compatible mode is the input associated with the presence of the MRI device.

23. The device of claim 12, wherein the processor is further configured to determine that the implantable medical device is no longer in the presence of the MRI device and reconfigure, in response to the determination, the sensing configuration of the sensing module to sensing parameters used prior to receiving the input associated with the presence of the MRI device.

24. The device of claim 12, wherein the sensing module, using the adjusted sensing configuration, senses signals that include noise caused by the interfering signal of the MRI device without clipping an amplitude of the sensed signals.

25. A non-transitory computer-readable medium comprising instructions that, when executed by a processor, cause the processor to:
receive an input associated with a presence of a magnetic resonance imaging (MRI) device that generates an interfering signal;
adjust, in response to receiving the input, a sensing configuration of a sensing module of an implantable medical device by decreasing a gain of the sensing module to reduce a likelihood of clipping of sensed signals that include noise caused by the interfering signal; and
sense signals using the adjusted sensing configuration while in the presence of the MRI device.

26. The non-transitory computer-readable medium of claim 25, wherein the instructions cause the processor to increase an input range of the sensing module to reduce the likelihood of clipping of sensed signals that include noise caused by the interfering signal.

27. The non-transitory computer-readable medium of claim 25, wherein the instructions cause the processor to sense, using the adjusted sensing configuration, signals that include noise caused by the interfering signal of the MRI device without clipping an amplitude of the sensed signals.

* * * * *